United States Patent [19]

Farnham

[11] Patent Number: 5,347,058
[45] Date of Patent: Sep. 13, 1994

[54] PROCESS FOR THE PRODUCTION OF FLUORINATED OLEFINS

[75] Inventor: William B. Farnham, Hockessin, Del.

[73] Assignee: E. I. Du Pont de Nemours and Company, Wilmington, Del.

[21] Appl. No.: 163,497

[22] Filed: Dec. 7, 1993

[51] Int. Cl.$^5$ .............. C07C 17/33; C07C 21/18; C07C 21/185; C07C 21/14

[52] U.S. Cl. .............. 570/142; 558/461; 562/825; 568/685; 570/135; 570/136; 570/137

[58] Field of Search .............. 570/142, 136, 135, 137; 562/825; 558/461; 568/685

[56] References Cited

U.S. PATENT DOCUMENTS

| | | | |
|---|---|---|---|
| 2,704,776 | 3/1955 | La Zerte et al. | 570/142 |
| 3,549,698 | 12/1970 | Coon | 549/531 |
| 4,400,546 | 8/1983 | Rammelt et al. | 570/142 |
| 5,162,594 | 11/1992 | Krespan | 570/136 |

FOREIGN PATENT DOCUMENTS

| | | | |
|---|---|---|---|
| 287219 | 10/1988 | European Pat. Off. | 570/136 |
| 2026677 | 1/1971 | Fed. Rep. of Germany | 549/531 |
| 904877 | 9/1962 | United Kingdom | 549/531 |
| WO93/20085 | 10/1993 | World Int. Prop. O. | |

OTHER PUBLICATIONS

LaZerte, J. D. et al, *J. Am. Chem. Soc.*, 75, 4525–4528, 1953.

*Primary Examiner*—Joseph E. Evans

[57] ABSTRACT

Fluorinated olefins are produced by thermolysis of a silyl ester of a fluorinated aliphatic carboxylic acid in the presence of a catalyst which provides fluoride ion, such as potassium fluoride. The fluorinated olefins are useful as monomers and chemical intermediates.

16 Claims, No Drawings

PROCESS FOR THE PRODUCTION OF FLUORINATED OLEFINS

FIELD OF THE INVENTION

Disclosed herein is a process for the production of fluorinated olefins, which comprises thermolyzing a silyl ester of a fluorinated aliphatic carboxylic acid in the presence of an alkali metal fluoride. The resulting olefins are useful as monomers for polymerization or as chemical intermediates.

TECHNICAL BACKGROUND

Fluorinated olefins, particularly those containing a trifluorovinyl group, are useful as monomers and as chemical intermediates for the synthesis of organic compounds, such as pharmaceuticals. Such olefins have been made by a variety of methods, for instance the pyrolysis of a fluorinated aliphatic carboxylic acid metal salt, J. D. LaZerte, et al., J. Am. Chem. Soc., vol. 75, p. 4525–4528 (1953).

WO 93/20085 reports the preparation of trifluorovinyl ethers by the thermolysis of compounds containing the grouping $-O(C_2F_4)CO_2Si$. Only trifluorovinyl ethers are prepared or mentioned in this patent.

SUMMARY OF THE INVENTION

This invention concerns a process for the production of fluorinated olefins, comprising, heating to a temperature of 150° C. to 400° C. a compound of the formula $R^1R^2CFCR^4R^5C(O)OSiR^3_3$ in the presence of a thermolysis catalyst, wherein:

$R^1$ and $R^2$ are each independently fluorine, hydrocarbyl or substituted hydrocarbyl;
$R^3$ is hydrocarbyl, substituted hydrocarbyl, or oxysilyl; $R^4$ is fluorine or perfluoroalkyl; and
$R^5$ is hydrogen or fluorine;
and provided that when $R^4$ is fluorine, said temperature is 200° C. to 400° C.

DETAILS OF THE INVENTION

Described herein is a process for the production of fluorinated olefins, by thermolysis of a silyl ester of a fluorinated aliphatic carboxylic acid of the formula $R^1R^2CFCR^4R^5C(O)OSiR^3_3$. From this, an olefin of the formula $R^1R^2CF=CR^4R^5$ is made, although during the reaction the double bond of the olefin may migrate (if possible) to an internal position (see Example 3). In preferred silyl esters (and the resulting olefins, assuming no double bond migration): $R^1$, $R^4$ and $R^5$ are fluorine, and $R^2$ is alkyl, preferably fluorine substituted alkyl, and more preferably perfluoroalkyl, and especially preferably perfluoro-n-alkyl, and very preferably trifluoromethyl; or $R^4$ and $R^5$ are fluorine, and $R^1$ and $R^2$ are each independently perfluoroalkyl, more preferably both $R^1$ and $R^2$ are perfluoro-n-alkyl; or $R^1$, $R^2$ and $R^5$ are fluorine and $R^4$ is trifluoromethyl; or $R^1$, $R^2$, $R^4$ and $R^5$ are fluorine; or $R^1$ and $R^4$ are fluorine, $R^2$ is trifluoromethyl, and $R^5$ is hydrogen; or $R^1$ and $R^2$ are fluorine, $R^4$ is trifluoromethyl, and $R^5$ is hydrogen. In all cases, it is preferred if $R^1$, $R^2$ and $R^4$ each independently contain 1 to 20 carbon atoms (assuming they are not fluorine).

By hydrocarbyl herein is meant a univalent radical containing only carbon and hydrogen. By a substituted hydrocarbyl radical is meant a hydrocarbyl group containing one or more substituents which are inert under the process conditions, except that one or more of the substituents may be a grouping such as $-CF_2CF_2C(O)OSiR^3_3$, wherein $R^3$ is as defined above. In other words, the silyl ester containing molecule may be "di- or higher-functional" with regard to the number of silyl esters which will react to form olefin groups. Useful substituents include, but are not limited to, fluoro, ether [between (substituted) hydrocarbyl segments], ester, sulfonyl fluoride, chloro, bromo, nitrile, sulfone [between (substituted) hydrocarbyl segments], sulfonate ester, and iodo. Preferred substituents are fluoro, ether, chloro, bromo, iodo, sulfonyl fluoride, nitrile, or perfluoroalkyl groups containing one or two hydrogen atoms.

$R^3$ is a radical which is bound to the silicon atom of the silyl ester. Preferred $R^3$ are alkyl containing 1 to 20 carbon atoms and phenyl, and an especially preferred $R^3$ is phenyl and alkyl containing 1 to 4 carbon atoms. In a more preferred silyl ester, all of $R^3$ are methyl. $R^3$ may also be oxysilyl. By an oxysilyl group is meant the $-OSi-$ group in which the free valencies of the silicon can be bound to a hydrocarbyl, substituted hydrocarbyl or additional oxysilyl groups.

A thermolysis catalyst, which is a source of fluoride ion, is needed for this process. Metal fluorides are sources of fluoride ions, and alkali metal fluorides are preferred catalysts, and potassium fluoride is more preferred. Other sources of fluoride ions are perfluorocarboxylate anions. When heated to the process temperature, these compounds are believed to decarboxylate and yield the corresponding metal fluoride. When the reaction is carried out in the gas phase, it is preferred to have a relatively large surface area of fluoride catalyst over which the vapor will pass. A metal fluoride may be, for example, in the form of a powder, a coating on an inert substrate or in pellet form. The silyl ester of a fluorinated aliphatic carboxylic acid must contact the thermolysis catalyst at the process temperature. Such contacting may be carried out while the silyl ester is in the liquid phase (either as a neat liquid or in solution) or in the gas phase, preferably the gas phase. The weight ratio of catalyst to silyl ester used is not critical, and can range from 100:1 to 0.001:1. Typically it is 0.1:1 to 0.04:1.

The process is carried out at a temperature of about 150° C. to about 400° C., preferably about 220° C. to about 300° C. Useful contact times (between the silyl ester and catalyst) include about 5 sec. to 5 min. Generally speaking, the higher the temperature, the less contact time needed. Water and oxygen should be absent as they lower yields. A convenient method of accomplishing this is to carry out the reaction under an inert gas such as nitrogen or argon. The silyl ester of a fluorinated aliphatic carboxylic acid can be made by various methods known to the artisan. For instance, the acyl fluoride of the corresponding fluorinated aliphatic carboxylic acid can be reacted with a siloxane to form the silyl ester, see for instance patent application WO 93/20085.

The fluorinated olefins made herein may be used as monomers in a free radically catalyzed (co)polymerization to form homopolymers or copolymers, particularly if the fluorinated olefin is a terminal olefin. Preferred fluorinated olefins for polymerization are tetrafluoroethylene and hexafluoropropylene, the former polymerized by itself to form homopolymers, and both polymerized with other monomers to form copolymers. Such polymerizations are known to the artisan, see for instance H. Mark et al., Ed., Encyclopedia of Polymer Science and Engineering, vol. 7, John Wiley & Sons, New York, 1987, p. 257–269; ibid., vol. 16, 1989, p. 577–648, both of which are hereby included by reference.

In the Examples "GC" is gas chromatography.

EXPERIMENT 1

Preparation of $CF_3CF_2CO_2SiMe_3$

A 200 mL Hastelloy ® pressure vessel was heated for 6 hr at 150° C. under a nitrogen purge. At room temperature, the vessel was charged with potassium trimethylsilanolate (0.65 g, 5.1 mmol) and hexamethyldisiloxane (81 g, 0.50 tool) and then sealed, cooled and evacuated. Pentafluoropropionyl fluoride (47.4 g, 0.27 mol) was transferred from a cycinder to the pressure vessel. Once sealed, it was heated at 125° C. (barricade). The pressure rapidly increased to 1.79 MPa and then dropped to 0.62 MPa during a 1.5 hr period. The pressure vessel was heated for a total of 24 hr. The cooled pressure vessel was pressurized with nitrogen and the contents were transferred to a dried bottle. The crude product was transferred under vacuum and subsequently fractionated by spinning band distillation to remove most of the trimethylsilyl fluoride. The remaining 100 g of colorless liquid was a mixture of three components: trimethylsilyl pentafluoropropionate (49.7%), hexamethyldisiloxane (42.6%), and trimethylsilyl fluoride (7.6%) as determined by GC analysis, $^1H$ and $^{19}F$ NMR analyses. $^{19}F$ NMR($CDCl_3$): −83.4 (s, $CF_3$), −122.28 (s, $CF_2$), −158.2 (m, SiF). $^1H$ NMR: 0.40 (s, $CO_2SiMe_3$), 0.22 (d, $Me_3SiF$), and 0.06 (s, $Me_6Si_2O$). GC/MS analysis of a previously prepared sample of $CF_3CF_2CO_2SiMe_3$ featured a component with m/z@220.989868 (calcd for$C_5H_6F_5SiO_2$=221.005722), consistent with M—$CH_3$.

EXAMPLE 1

Thermolysis of $CF_3CF_2CO_2Si(CH_3)_3$

A 40 cm×1.3 cm Hastelloy ® tube, fitted with ports for the introduction of inert gas, thermocouple, and liquid samples, was charged with a mixture of 3 mm glass beads (20 g) and spray-dried potassium fluoride (3 g) and mounted vertically in a muffle furnace. The fixed bed was held in place by a stainless steel screen, and clean glass beads were placed above the catalyst-containing portion of the tube. Approximately 18 cm of the tube'length (ca. 24 cm$^3$) was in the heated zone. Dry nitrogen was passed through the tube at 14.5 cm$^3$/min while the tube was maintained at 225° C. for 18 hr. Liquids were added by a syringe driven by a syringe pump set to deliver 0.1 mL/min. Exit gases were passed through two glass traps (in series) fitted with coarse dispersion frits. Each trap was charged with a solution of bromine (1.4 mL, 4.1 g) in $CCl_4$ (50 mL), and the second trap was cooled at 0° C. while the first was operated at ambient temperature (20°–23° C.).

A 3.14 g sample of the above trimethylsilyl ester preparation (1.57 g, 6.65 mmol of $CF_3CF_2CO_2Si(CH_3)_3$) was added to the reactor maintained at 224°–226° C. during a 0.5 hr period while the exit gases were passed through the $Br_2/CCl_4$ solutions. After the addition was complete, the column inert gas flow was maintained for an additional 45 min. Excess bromine was quenched by addition of aqueous sodium sulfite at 0° C. with shaking. Decafluorobiphenyl was added as an internal standard, and the dried organic layer was analyzed by GC and $^{19}F$ NMR which showed 1,2-dibromo-tetrafluoroethane as the only detectable organofluorine product obtained in 48% yield (based on silyl ester added). Trimethylsilyl fluoride was obtained in similar quantities. Trimethylsilyl pentafluoropropionate is thus cleanly converted to tetrafluoroethylene, carbon dioxide, and trimethylsilyl fluoride.

EXAMPLE 2

Thermolysis of $CF_3CF_2CO_2Si(CH_3)_3$

A 40 cm×1.3 cm Hastelloy ® tube, fitted with ports for the introduction of inert gas, thermocouple, and liquid samples, was charged with a mixture of 3 mm glass beads (20 g) and spray-dried potassium fluoride (3 g) and mounted vertically in a muffle furnace. The fixed bed was held in place by a stainless steel screen, and clean glass beads were placed above the catalyst-containing portion of the tube. Approximately 18 cm of the tube's length (ca. 24 cm$^3$) was in the heated zone. Dry nitrogen was passed through the tube at 14.5 cm$^3$/min while the tube was maintained at 225° C. for 18 hr. Liquids were added by a syringe driven by a syringe pump set to deliver 0.1 mL/min. Exit gases were passed through two glass traps (in series) fitted with coarse dispersion frits. Each trap was charged with a solution of bromine (1.4 mL, 4.1 g) in $CCl_4$ (50 mL), and the second trap was cooled at 0° C. while the first was operated at ambient temperature (20°–23° C.).

A 3.00 g sample of the above trimethylsilyl ester preparation (1.50 g, 6.35 mmol of $CF_3CF_2CO_2Si(CH_3)_3$) was added to the reactor maintained at 250° C. during a 0.5 hr period while the exit gases were passed through the $Br_2/CCl_4$ solutions. After the addition was complete, the column inert gas flow was maintained for an additional 45 min. Excess bromine was quenched by addition of aqueous sodium sulfite at 0° C. with shaking. Decafluorobiphenyl (0.21 g) was added as an internal standard, and the dried organic layer was analyzed by GC and $^{19}F$ NMR which showed 1,2-dibromo-tetrafluoroethane as the only detectable organofluorine product obtained in ca. 100% yield (based on silyl ester added). Trimethylsilyl fluoride was obtained in similar quantities. Trimethylsilyl pentafluoropropionate is thus cleanly converted to tetrafluoroethylene, carbon dioxide, and trimethylsilyl fluoride.

EXPERIMENT 2

Preparation of $C_7F_{15}CO_2Si(CH_3)_3$

A sample of perfluorooctanoic acid (13.0 g, 31.4 mmol) was placed in a 3-neck round bottom flask and treated with hexamethyldisilazane (2.9 g, 18.0 mmol) in portions. Some gas evolution took place, and the exotherm was controlled by means of an ice bath. Another portion of hexamethyldisilazane (2.9 g, 18 mmol) was added to the heterogeneous mixture, and the flask was immersed in an oil bath at ca 140° C. in order to drive the reaction to completion. The mixture was maintained at 150° C. for 0.5 hr and then cooled to 25° C. The liquid was separated from a small quantity of remaining solid and distilled, first at atmospheric pressure to remove most of the excess hexamethyldisilazane, and then at 20 mm Hg to collect the product with bp=75° C. There was obtained 11.7 g of colorless liquid homogeneous by GC. $^{19}F$ NMR ($CDCl_3$): −81.4 (m, $CF_3$), −119.08 (t, J=10.9 Hz, $CF_2C(O)$), −122.1 (s, $CF_2$), −122.5 (s, $CF_2$), −123.2 (s, two $CF_2$), −126.7 (m, $CF_2$). $^1H$ NMR ($CDCl_3$): 0.38 (s, $CH_3$).

EXAMPLE 3

Thermolysis of $C_7F_{15}CO_2Si(CH_3)_3$

A 1.50 g sample of the title silyl ester (3.08 mmol) was added to the previously described thermolysis bed containing potassium fluoride and glass beads and maintained at 225° C. Addition was carried out over a 10 min period, and supplementary nitrogen flow was fixed at 13.5 mL/min. Products were collected in a tared gas trap cooled at −78° C. The trap was warmed to 25° C. and $CO_2$ allowed to escape through an outlet. Remaining liquid (0.7 g) was analyzed by GC which showed no detectable starting trimethylsilyl ester. $^{19}F$ NMR ($CDCl_3$) was consistent with a mixture of perfluorinated heptenes in the following ratio: 1-heptene/t-2-heptene/c-2-heptene=78/17/5. Characteristic shifts for the olefinic CF groups of the major product were −87.5, −104.8, and −189.2, while $CF_3$ signals of the minor products appeared at −69.1 (trans) and −65.6 (cis).

EXAMPLE 4

Thermolysis of $C_7F_{15}CO_2Si(CH_3)_3$

A 1.50 g sample of the title silyl ester (3.08 mmol) was added to the previously described thermolysis bed containing potassium fluoride and glass beads and maintained at 250° C. Addition was carried out over a 10 min period, and supplementary nitrogen flow was fixed at 13.5 mL/min. Products were collected in a simple tared gas trap cooled at −78° C. The trap was warmed to 25° C. and $CO_2$ allowed to escape through an outlet. Remaining liquid (1.30 g) was analyzed by GC which showed no detectable starting trimethylsilyl ester. $^{19}F$ NMR ($CDCl_3$) was consistent with a mixture of perfluorinated heptenes in the following ratio: 1-heptene/t-2-heptene/c-2-heptene=65/28/7. Characteristic shifts for the olefinic CF groups of the major product were −87.5, −104.8, and −189.2, while $CF_3$ signals of the minor products appeared at −69.1 (trans) and −65.6 (cis).

EXPERIMENT 3

Preparation of $CF_3CF_2CF_2CO_2Si(CH_3)_3$

A commercial sample of perfluorobutanoic acid (21.4 g, 100 mmol) was placed in a 3-neck round bottom flask (equipped with reflux condenser, dropping funnel, and connected to a dry nitrogen line) and treated with hexamethyldisilazane (8.1 g, 50 mmol) in portions. Some gas evolution took place, and the exotherm was controlled by means of an ice bath. The mixture was stirred at 50° C. for 18 hr, heated at reflux for 3.5 hr, and allowed to cool. The resulting top liquid layer was transferred under vacuum (0.1 mm) to afford 17.8 g of liquid which was fractionated (1 atm). A fraction (9.0 g), bp 106 −108° C., was >99% pure by GC analysis. $^{19}F$ NMR ($CDCl_3$): −81.43 (t, J=8.3 Hz), −120.02 (q, J=8.4 Hz), −127.7 (s); $^1H$ NMR: 0.38 (s). Upon treatment with additional hexamethyldisilazane (5.0 mL) at reflux, the solid ammonium carboxylate obtained from the reaction provided an additional 9.4 g of trimethylsilyl ester.

EXAMPLE 5

Thermolysis of $CF_3CF_2CF_2CO_2Si(CH_3)_3$

Pelletized potassium fluoride (ca. 4 mm diameter×4 mm length) containing a small but undetermined amount of adventitious water was processed as follows. Pellets were placed in a drying boat contained in a glass tube which was then mounted in a horizontal muffle furnace. The tube was subjected to continuous vacuum (0.1 mm) while it was heated gradually to 350° C. over a ca 3 hr. period. The pellets were transferred to a dry box and fractured into irregular particles (ca. 1–2 mm average dimension). A 21.8 g charge was held in place by a stainless steel screen in a 40 cm×1.3 cm Hastelloy tube fitted with ports for the introduction of inert gas, thermocouple, and liquid samples and mounted vertically in a muffle furnace. Approximately 18 cm of the tube's length was in the heated zone.

The reactor was purged with nitrogen (30 mL/min) and heated to 350° C. for 2.5 hr. After equilibration at 250° C., the flow was reduced to 15 mL/min, and a sample of the title silyl ester (1.82 g, 6.36 mmol) was added to the reactor over a 15 min interval while the exit gas was passed through two traps (at −78° C.) in series. All the condensables were collected in the first trap. The nitrogen purge was turned off, and the trap contents were allowed to distill into the second trap. There remained less than 0.025 mL of liquid in the first trap, indicating >99% conversion of the silyl ester. The volume of liquid product (1.1 mL) was essentially that expected for additive volumes of hexafluoropropene (0.95 g) and trimethylsilyl fluoride (0.59 g). $^{19}F$ NMR ($CDCl_3$) (vacuum line sample preparation) showed signals for hexafluoropropene (−68.83, m, $CF_3$), −91.7, −105.8, and −192.25 (m, CF) and trimethylsilyl fluoride (−158.3) only. No signals for HFP dimers or $C_3F_7H$ were observable.

What is claimed is:

1. A process for the production of fluorinated olefins, comprising, heating to a temperature of about 150° C. to about 400° C. a compound of the formula $R^1R^2CFCR^4R^5C(O)OSiR^3_3$, in the presence of a thermolysis catalyst, wherein:

$R^1$ and $R^2$ are each independently fluorine, hydrocarbyl or substituted hydrocarbyl;

$R^3$ is hydrocarbyl, substituted hydrocarbyl, or oxysilyl; $R^4$ is fluorine or perfluoroalkyl; and $R^5$ is hydrogen or fluorine; and provided that when $R^4$ is fluorine, said temperature is 200° C. to 400° C.

2. The process as recited in claim 1 wherein $R^1$, $R^4$ and $R^5$ are fluorine, and $R^2$ is perfluoroalkyl.

3. The process as recited in claim 2 wherein $R^2$ is perfluoro-n-alkyl.

4. The process as recited in claim 1 wherein $R^4$ and $R^5$ are fluorine, and $R^1$ and $R^2$ are independently perfluoroalkyl.

5. The process as recited in claim 1 wherein:

$R^1$, $R^4$ and $R^5$ are fluorine and $R^2$ is trifluoromethyl; or $R^1$, $R^2$ and $R^5$ are fluorine and $R^4$ is trifluoromethyl.

6. The process as recited in claim 1 wherein said temperature is about 220° C. to about 300° C.

7. The process as recited in claim 5 wherein said temperature is about 220° C. to about 300° C.

8. The process as recited in claim 1 wherein each $R^3$ is alkyl containing 1 to 20 carbon atoms.

9. The process as recited in claim 7 wherein each $R^3$ is methyl.

10. The process as recited in claim 7 wherein each $R^3$ is alkyl containing 1 to 20 carbon atoms.

11. The process as recited in claim 1 wherein said catalyst is an alkali metal fluoride.

12. The process as recited in claim 11 wherein said alkali metal fluoride is potassium fluoride.

13. The process as recited in claim 9 wherein said catalyst is potassium fluoride.

14. The process as recited in claim 1 wherein:

$R^1$ and $R^4$ are fluorine, $R^2$ is trifluoromethyl and $R^5$ is hydrogen; or $R^1$ and $R^2$ are fluorine, $R^4$ is trifluoromethyl and $R^5$ is hydrogen.

15. The process as recited in claim 1 wherein a substituent is one or more of fluoro, ether, chloro, bromo, iodo, sulfonyl fluoride, nitrile, or perfluoroalkyl groups containing one or two hydrogen atoms.

16. The process as recited in claim 1 wherein $R^1$, $R^2$ $R^4$ and $R^5$ are fluorine.

* * * * *